(12) United States Patent
Cheng

(10) Patent No.: US 9,168,187 B2
(45) Date of Patent: Oct. 27, 2015

(54) FASTENING STRAP FOR DISPOSABLE ABSORBING ARTICLES, METHOD FOR MANUFACTURING THE SAME AND DISPOSABLE ABSORBING ARTICLES INCLUDING THE SAME

(71) Applicant: Taiwan Paiho Limited, Chang Hwa Hsien (TW)

(72) Inventor: Allen Cheng, Chang Hwa Hsien (TW)

(73) Assignee: TAIWAN PAIHO LIMITED, Ho Mei Town, Chang Hwa Hsien (TW)

( * ) Notice: Subject to any disclaimer, the term of this patent is extended or adjusted under 35 U.S.C. 154(b) by 133 days.

(21) Appl. No.: 13/871,018

(22) Filed: Apr. 26, 2013

(65) Prior Publication Data
US 2013/0289514 A1 Oct. 31, 2013

(30) Foreign Application Priority Data
Apr. 27, 2012 (TW) .............................. 101115050 A

(51) Int. Cl.
*A61F 13/62* (2006.01)
*A61F 13/56* (2006.01)
*B32B 37/16* (2006.01)

(52) U.S. Cl.
CPC ............ *A61F 13/625* (2013.01); *A61F 13/5622* (2013.01); *A61F 13/62* (2013.01); *A61F 13/622* (2013.01); *B32B 37/16* (2013.01); *Y10T 24/27* (2015.01)

(58) Field of Classification Search
CPC ... A61F 13/5622; A61F 13/62; A61F 13/622; A61F 13/625

USPC .......................................................... 604/391
See application file for complete search history.

(56) References Cited

U.S. PATENT DOCUMENTS

| | | | |
|---|---|---|---|
| 5,108,384 A * | 4/1992 | Goulait ......................... | 604/390 |
| 5,176,670 A * | 1/1993 | Roessler et al. .............. | 604/391 |
| 5,953,797 A * | 9/1999 | Provost et al. ................. | 24/452 |
| 6,736,804 B1 * | 5/2004 | Robertson et al. ........ | 604/385.13 |
| 7,291,371 B2 * | 11/2007 | Verhaert ...................... | 428/40.1 |
| 7,722,589 B2 * | 5/2010 | Fitts et al. ................ | 604/385.22 |
| 7,811,272 B2 * | 10/2010 | Lindsay et al. ............... | 604/389 |
| 2002/0022108 A1 * | 2/2002 | Krantz et al. ................. | 428/100 |
| 2003/0055394 A1 * | 3/2003 | Gibbs .......................... | 604/389 |
| 2003/0069557 A1 * | 4/2003 | Driskell et al. ............ | 604/385.3 |
| 2003/0083635 A1 * | 5/2003 | Gibbs ...................... | 604/385.04 |
| 2003/0100880 A1 * | 5/2003 | Magee et al. ................. | 604/389 |
| 2003/0121128 A1 * | 7/2003 | Vanbenschoten et al. ...... | 24/452 |

(Continued)

OTHER PUBLICATIONS

Search report issued in corresponding European patent application No. 13165418.8, dated Jul. 9, 2013.

(Continued)

*Primary Examiner* — Susan Su
(74) *Attorney, Agent, or Firm* — Bacon & Thomas, PLLC

(57) ABSTRACT

The present invention provides a fastening strap for disposable absorbing articles comprising a fabric backing and a hook strap on which a plurality of hooks are formed for releasably engaging loops on a loop strap of the disposable absorbing articles, wherein the hook strap is secured directly to the fabric backing by means of fusion bonding to form patterns on the fastening strap to thereby producing a fastening strap for disposable absorbing articles in a more simple process without using any adhesive. A method for manufacturing this fastening strap and a disposable absorbing article including this fastening strap are also provided.

6 Claims, 6 Drawing Sheets

(56) References Cited

U.S. PATENT DOCUMENTS

| | | | |
|---|---|---|---|
| 2004/0073187 A1* | 4/2004 | Karami | 604/391 |
| 2004/0153046 A1* | 8/2004 | Ito et al. | 604/391 |
| 2004/0238095 A1* | 12/2004 | Johnson | 156/66 |
| 2004/0258902 A1* | 12/2004 | Seth et al. | 428/315.7 |
| 2004/0261230 A1* | 12/2004 | Neeb et al. | 24/451 |
| 2005/0079321 A1* | 4/2005 | Tuman et al. | 428/100 |
| 2005/0283954 A1* | 12/2005 | Erdman et al. | 24/442 |
| 2007/0275622 A1* | 11/2007 | Masuda et al. | 442/327 |
| 2008/0097368 A1* | 4/2008 | Molander | 604/391 |
| 2011/0313389 A1* | 12/2011 | Wood et al. | 604/391 |
| 2012/0101469 A1* | 4/2012 | Sperl | 604/391 |

OTHER PUBLICATIONS

Search report issued in corresponding European patent application No. 13165418.8, dated Sep. 23, 2013.

* cited by examiner

FASTENING STRAP FOR DISPOSABLE ABSORBING ARTICLES, METHOD FOR MANUFACTURING THE SAME AND DISPOSABLE ABSORBING ARTICLES INCLUDING THE SAME

FIELD OF THE INVENTION

The present invention relates generally to a fastening strap for a disposable absorbing article, and more specifically to a fastening strap for a disposable absorbing article with great softness that is produced by a simplified process without using any adhesive, a manufacturing method for making the fastening strap and a disposable absorbing article including the fastening strap.

BACKGROUND OF THE INVENTION

A hook-and-loop type fastener is a well know mechanical fastener and wildly used in disposable absorbing articles, such as diapers for babies and adults, to fasten the diaper around the waist of a wear's body. As illustrated in FIG. 1, a hook-and-loop type fastener utilized as a fastening device of a diaper 1 usually consists of two fastening straps 10 each secured to a lateral side of a first end of the diaper 1 respectively and a loop strap 20 provided on an outer face of a second end of the diaper 1. Each of the fastening strap 10 has a plurality of hooks 12 formed thereon for releasably engaging with the loops 22 formed on the loop strap 20 to fasten the diaper 1 on the wear's body. Traditional fastening strap 10, as illustrated in FIG. 2, usually includes a backing layer 14, a hook strap layer 16, and an adhesive layer 18 disposed between the backing layer 14 and the hook strap layer 16 to bond the backing layer 14 and the hook strap layer 16 together to form the fastening strap 10. The hook strap layer 16 is a plastic layer that includes a plastic substrate and a plurality of hooks 12 that is integrally formed on the substrate by means of a plastic injection process.

Because the traditional fastening strap 10 consists of three layers and the hook strap layer 16 is a plastic layer, it is too stiff for applications that suppleness of a fastening strap is a critical factor. For instance, when utilized in a diaper the fastening strap is used to keep the diaper in place about the wearer and thus has an intimate contact with the skin of the wear. Therefore, if the fastening strap does not have sufficient suppleness, the wearer of the diaper may feel uncomfortable and even may leave marks on the skin of the wearer.

Additionally, because the traditional fastening strap 10 uses an adhesive layer to bind the hook strap 16 and the backing layer 14 together, the manufacturing process is thus complicated. Moreover, because an adhesive layer 18 is used to bind the hook strap 16 and the backing layer 14 the manufacturing cost is inevitably increased and so is the sale price, and thus making the fastening strap 10 less competitive in the market.

In view of the shortcomings of traditional fastening strap described above, there exists a need for a fastening strap for a disposable absorbing article that possess a sufficient fastening strength and a sufficient suppleness.

SUMMARY OF THE INVENTION

One object of the present invention is to provide a fastening strap for a disposable absorbing article that possess a sufficient fastening strength and a sufficient suppleness.

Another object of the present invention is to provide a fastening strap for a disposable absorbing article that is produced in a more environmental friendly and more simply way that has a higher yield, a lower manufacturing cost, and does not use any adhesive in the process and thus is suitable for mass production.

The above objects may be achieved by a fastening strap for a disposable absorbing article. According to one aspect of the present invention, the fastening strap for a disposable absorbing article comprises:

a fabric backing;

a plastic hook strap disposed on at least a portion of the fabric backing and having a plurality of hooks formed on a face facing away from the backing, wherein the plastic hook strap is directly bind to the fabric backing by means of a fusion bonding process, and binding patterns are formed on the fastening strap during the fusion bonding process to lower the overall stiffness of the fastening strap to provide a sufficient softness to the fastening strap.

Preferably, the fastening strap for a disposable absorbing article includes sealing portions at both lateral sides of the hook strap and the sealing portions are formed by performing a fusion bonding process along both lateral sides of the plastic hook strap to bind the lateral sides of the hook strap to the fabric backing so as to prevent the lateral sides of the hook strap from warping upwardly. Additionally, the fabric backing may be a non-woven fabric, and the fusion bonding process may be an ultrasonic welding process or a thermal welding process. The binding patterns may be a plurality of linear grooves that are parallel with each other and evenly spaced apart from each other. The binding patterns may be a matrix of circular or polygonal dimples.

A method of manufacturing a fastening strap for a disposable absorbing article is also provided and the method includes the steps of:

providing a web of fabric backing;

placing a plastic hook strap on at least a portion of the fabric backing, the plastic hook strap having a plurality of hooks integrally formed on a face thereof facing away from the fabric backing; and performing a fusion bonding process to the stacked plastic hook strap and fabric backing to allow the plastic melted from the plastic hook strap to penetrate into the fabric backing so as to directly fix the plastic hook strap to the backing, in the mean time, a number of binding patterns are formed on the fastening strap such that the overall stiffness of the fastening strap is lowered so as to provide a sufficient softness to the fastening strap.

Preferably, the method further comprises the step of performing a fusion bonding process along both lateral sides of the plastic hook strap to bind the lateral sides of the hook strap to the fabric backing so as to prevent the lateral sides of the hook strap from warping upwardly.

Preferably, the method further comprises a cutting step to cut the fastening strap into desired size and shape.

According to another embodiment, the fastening strap for a disposable absorbing article comprises:

a plastic hook strap including a plurality of hooks integrally formed on a face thereof; and two fabric side wings, which are disposed at two lateral sides of the plastic hook strap respectively and directly bonded thereto by performing a fusion bonding process on the stacked portions of lateral sides of the plastic hook strap and the two fabric side wings.

Preferably, the two fabric side wings may be non-woven fabric, and the fusion bonding process may be an supersonic welding process or a thermal welding process.

According to yet another embodiment, the fastening strap for a disposable absorbing article comprises:

a plastic hook strap including a plurality of hooks integrally formed on a face thereof;

two fabric side wings, which are overlaid at two lateral sides of the plastic hook strap respectively and directly bonded thereto by performing a fusion bonding process on the overlaid portions of lateral sides of the plastic hook strap and the two fabric side wings; and a connecting member having an adhesive film provided at a top face thereof and disposed on one of the fabric side wings such that a distal edge of the fabric side wing located at a substantially middle portion of the connecting member, and the connecting member is directly fixed to the fabric side wing at the substantially middle portion such that two end sides of the connecting member may be folded toward each other.

Preferably, the two fabric side wings and the connecting member may be non-woven fabric, and the fusion bonding process may be a supersonic welding process or a thermal welding process.

Another aspect of the present invention provides a disposable absorbing article comprising a front waist portion; a rear waist portion; a crotch portion extending between the front and the rear waist portions; a loop strap provided on an outer face of the front waist portion and having a plurality of loops formed thereon; and two fastening straps according to the embodiments described above, each of the fastening straps being attached to a lateral side of the rear waist portion for releasably engaging with the loops of the loop strap so as to fastening the disposable absorbing article on to a wear's body.

Features and objects of the present invention other than the above will become clear by reading the description of the present specification with reference to the accompanying drawings.

BRIEF DESCRIPTION OF THE DRAWINGS

For a more complete understanding of the present invention and the advantages thereof, reference is now made to the following description taken in conjunction with the accompanying drawings, wherein.

DETAILED DESCRIPTION OF THE INVENTION

Referring now to FIGS. 3-8, embodiments of the present invention are illustrated for describing a fastening strap for a disposable absorbing article and a diaper having the fastening strap attached thereon. It will be appreciated that although following discussions are provided with reference to a diaper, the scope of the present invention is not limited thereto, instead, the fastening strap of the present invention is equally applicable to other types of disposable absorbing articles.

Figure 1:
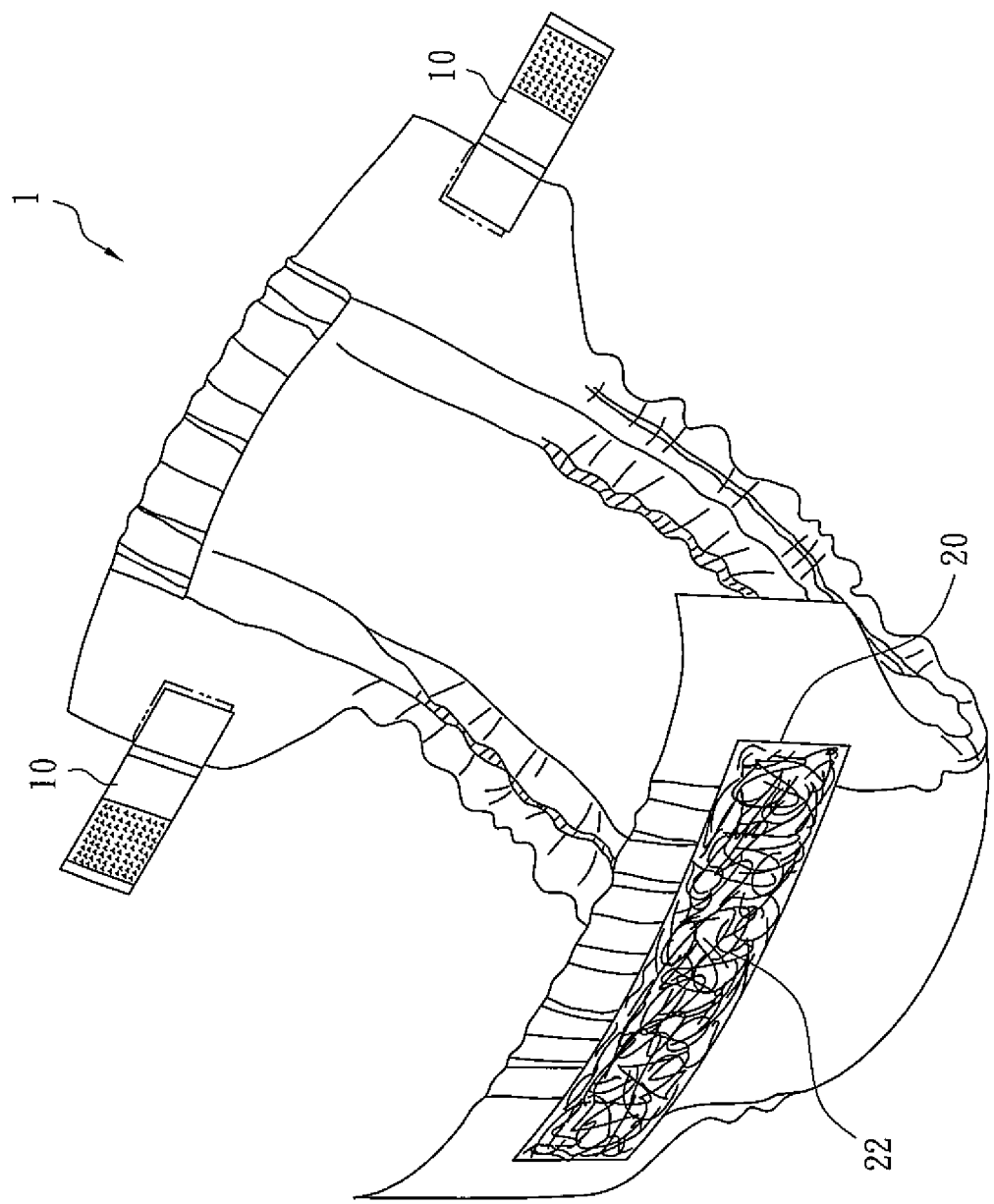
FIG. 1 is a schematic perspective view of a diaper having traditional fastening straps attached thereon.
Figure 2:
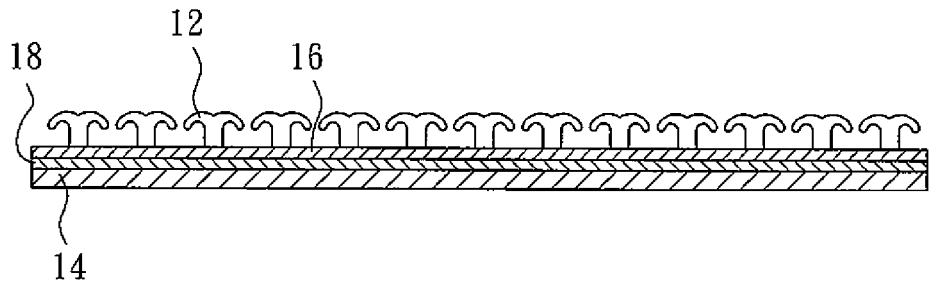
FIG. 2 is a schematic cross-sectional view of a traditional fastening strap.
Figure 3:
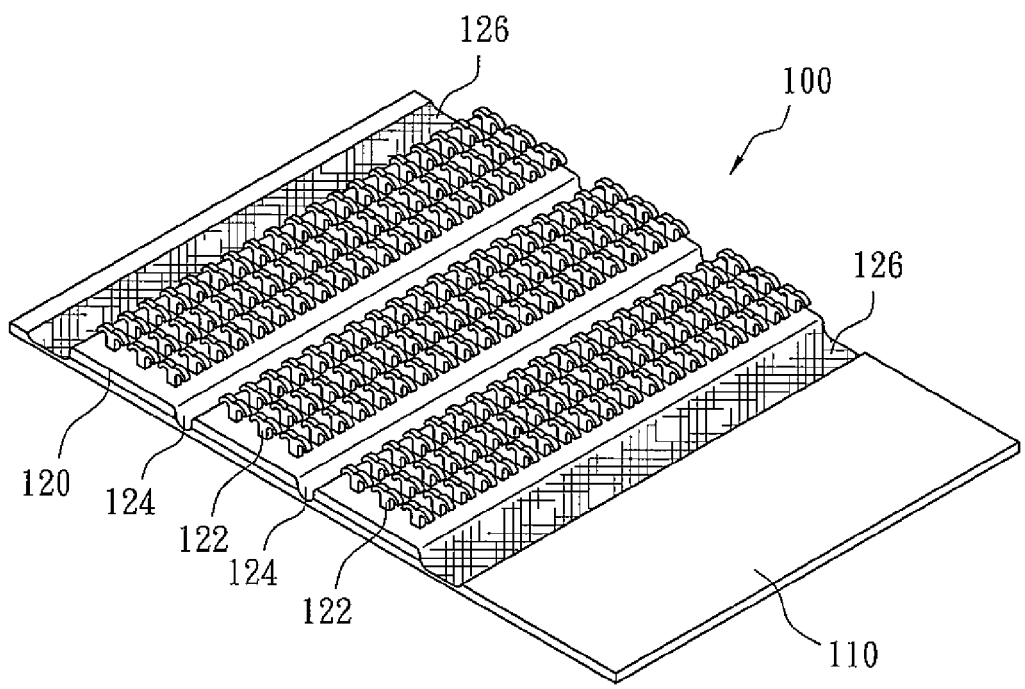
FIG. 3 is a schematic perspective view of a fastening strap for a disposable absorbing article according to an embodiment of a first aspect of the present invention.
Figure 4:
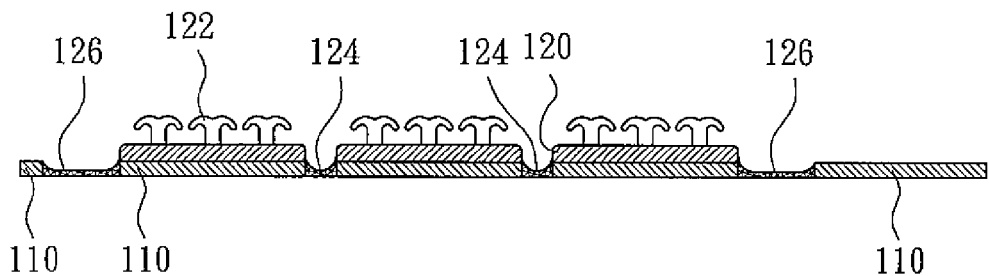
FIG. 4 is a schematic cross-sectional view of the fastening strap for a disposable absorbing article shown in FIG. 3.

Referring now to FIGS. 3 and 4, FIG. 3 a schematic perspective view of a fastening strap 100 for a disposable absorbing article (e.g. a diaper) according to an embodiment of a first aspect of the present invention; and FIG. 4 is a schematic cross-sectional view of the fastening strap 100 for a disposable absorbing article shown in FIG. 3.

Figure 5:
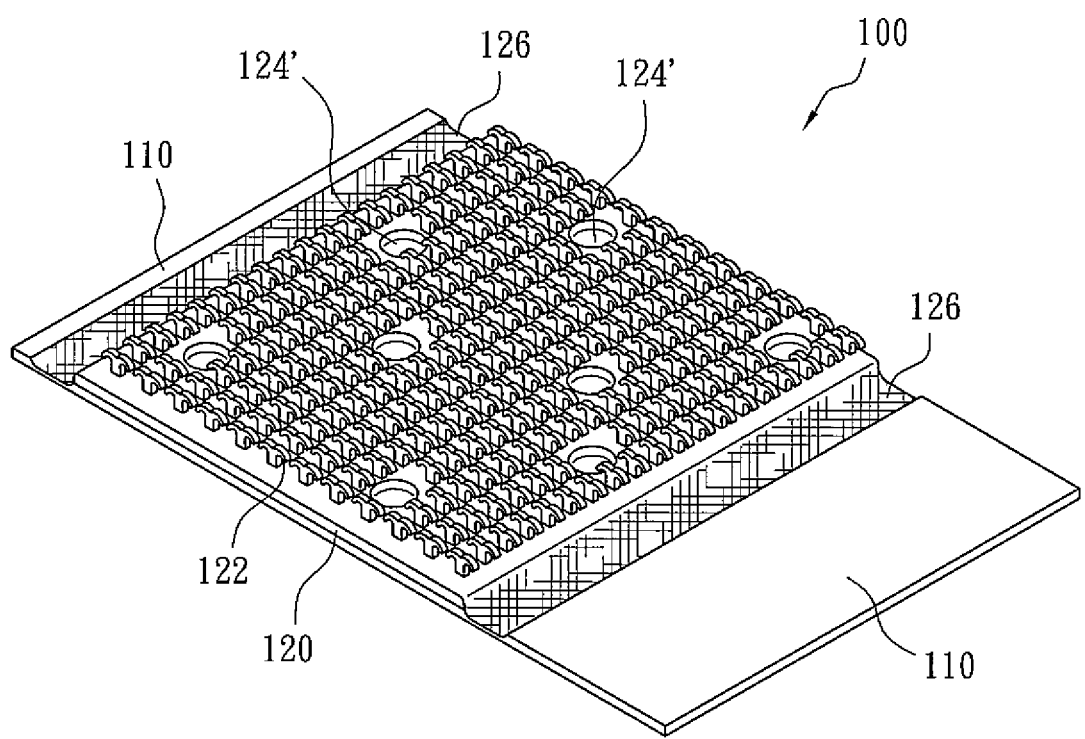
FIG. 5 is a schematic perspective view of a fastening strap for a disposable absorbing article according to another embodiment of a first aspect of the present invention.

As illustrated in FIGS. 3 and 4, the fastening strap 100 for a disposable absorbing article of the present invention mainly includes a fabric backing 110 and a plastic hook strap 120. Preferably, the fabric backing 110 is a non-woven fabric backing Alternatively, the fabric backing 110 may be made of other suitable fabric material. The plastic hook strap 120 is overlay on top of at least a portion of the fabric backing 110 and has a plurality of hook 122 integrally formed on a face facing away from the fabric backing 110. The plastic hook strap 120 is directly secured to the fabric backing 110 by means of a fusion bonding process, such as a supersonic welding process, a thermal welding process. During the fusion bonding process, binding patterns 124 are formed on the fastening strap 100 and in the embodiment illustrated in FIGS. 3 and 4, the binding patterns 124 are parallel linear grooves 124 that are evenly spaced from each other. According to another embodiment, the binding patterns 124 may be an array of circular dimples 124', as illustrated in FIG. 5, or polygonal dimples (not shown). Additionally, in order to prevent two later sides of the plastic hook strap 120 that are not welded to the fabric backing 110 from warping upwardly, sealing portions 126 are formed along the lateral sides of the plastic hook strap 120 by performing a welding process so as to fix the lateral sides of the plastic hook strap 120 to the fabric backing 110.

Figure 6A:
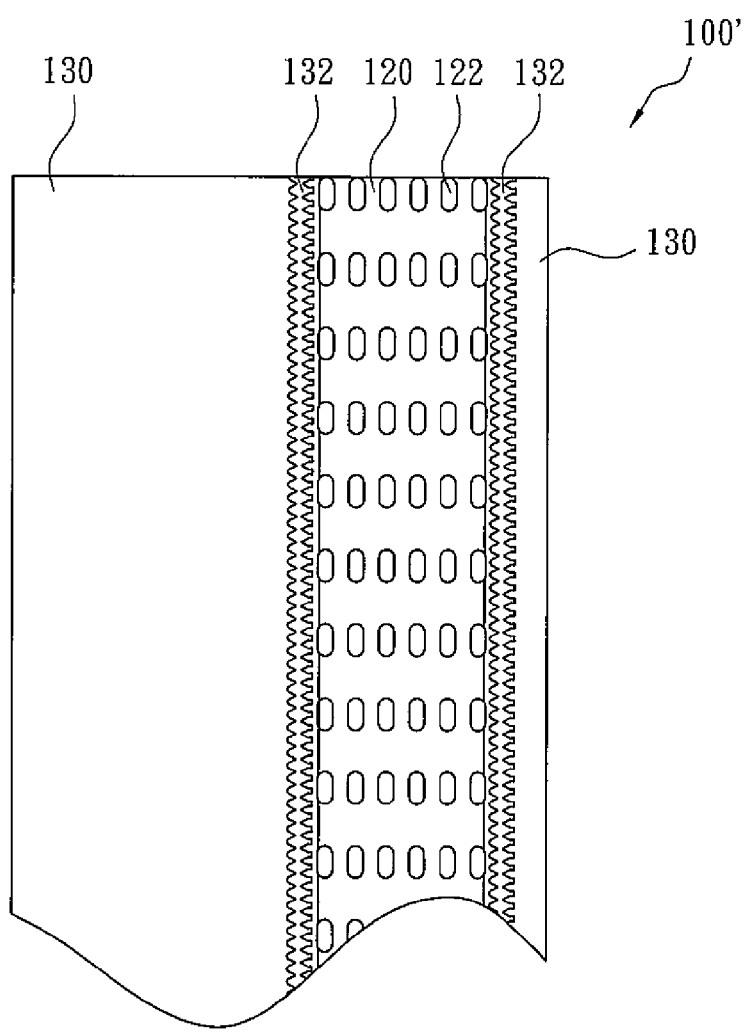
FIGS. 6a and 6b are schematic plane view and schematic cross-sectional view respectively which illustrate a fastening strap for a disposable absorbing article according to a second embodiment of the present invention.
Figure 6B:
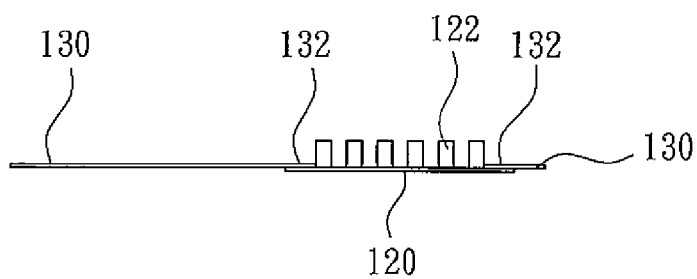

FIGS. 6a and 6b are schematic plane view and schematic cross-sectional view respectively, which illustrate a fastening strap 100' for a disposable absorbing article according to a second embodiment of the present invention. As illustrated in the drawings, the fastening strap 100' mainly includes a plastic hook strap 120 having a plurality of hooks 122 integrally formed on a face thereof, and two fabric side wings 130 with one fabric side wings 130 being overlaid on one side of the plastic hook strap 120 respectively and directly secured thereto by performing a fusion bonding process (e.g., a supersonic welding process or a thermal welding process) on overlaid portions 132 between the side wings 130 and the hook strap 120 so as to bind the side wings 130 directly to the sides of the plastic hook strap 120 to form the fastening strap 100'.

Figure 7A:
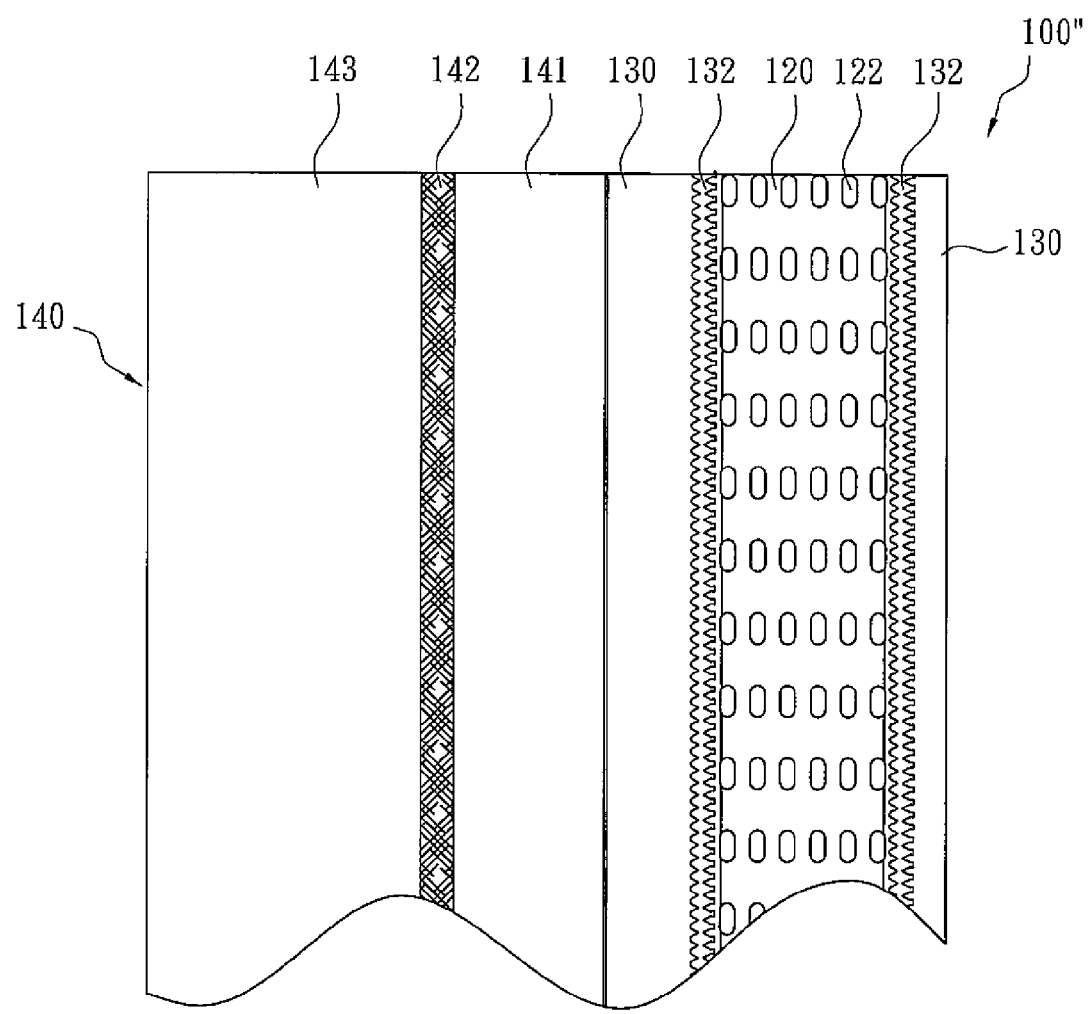
FIGS. 7a and 7b are schematic plane view and schematic cross-sectional view respectively illustrating a fastening strap for a disposable absorbing article according to a third embodiment of the present invention.
Figure 7B:
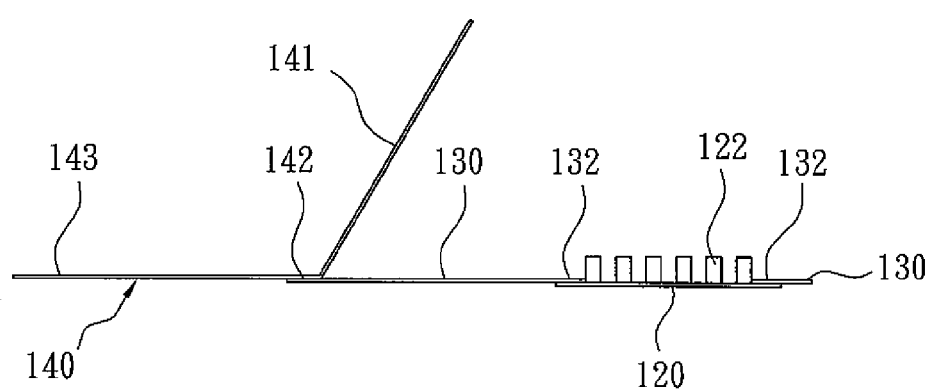

FIGS. 7a and 7b are schematic plane view and schematic cross-sectional view respectively, which illustrate a fastening strap 100" for a disposable absorbing article according to a third embodiment of the present invention. As illustrated in the drawings, the fastening strap 100" mainly includes a plastic hook strap 120 having a plurality of hooks 122 integrally formed on a face thereof, two fabric side wings 130 with one of which being overlaid on one side of the plastic hook strap 120 respectively and directly secured thereto by means of a fusion bonding press, and a connecting member 140 having an adhesive film 142 provided at a top face thereof and disposed on one of the fabric side wings 130 such that a distal free edge of the fabric side wing 130 located at a substantially middle portion of the connecting member 140. The connecting member 140 is directly secured to the fabric side wing 130 on which it is disposed at the substantially middle portion by means of a welding process such that two end sides 141, 143 of the connecting member 140 may be folded toward each other. The end sides 141, 143 of the connecting member 140 may be welded to a disposable absorbing article (e.g., a diaper) so as to attach the fastening strap 100" to the disposable absorbing article (e.g., a diaper).

Next, a process for making a fastening strap 100 for a disposable absorbing article according to the first embodiment of the present invention will be described. First, a web of fabric backing 110, such as a web of non-woven fabric or other suitable fabric material, is provided. Then, overlaying a hook strap 120 on top of at least one portion of the fabric backing 110, wherein the plastic hook strap 120 has a plurality of hook 122 integrally formed on a face thereof facing away from the fabric backing 110. Next, performing a fusion bonding process, such as a supersonic welding process, a thermal welding process and the like, to the overlaid plastic hook strap 120 and fabric backing 110 to allow the plastic melted from the plastic hook strap to penetrate into the fabric backing 110 so as to directly secure the plastic hook strap 120 to the backing 110, and in the mean time a number of binding patterns 124 are formed on the fastening strap 100 such that the overall stiffness of the fastening strap 100 is lowered so as to provide a sufficient softness to the fastening strap 100. Then, a fusion bonding process along both lateral sides of the plastic hook strap 100 is performed so as to bind the lateral sides of the hook strap 120 to the fabric backing 110 so as to prevent the lateral sides of the hook strap 120 from warping upwardly. Finally, cutting thus formed fastening strap 100 into desired sizes and shapes.

Figure 8:
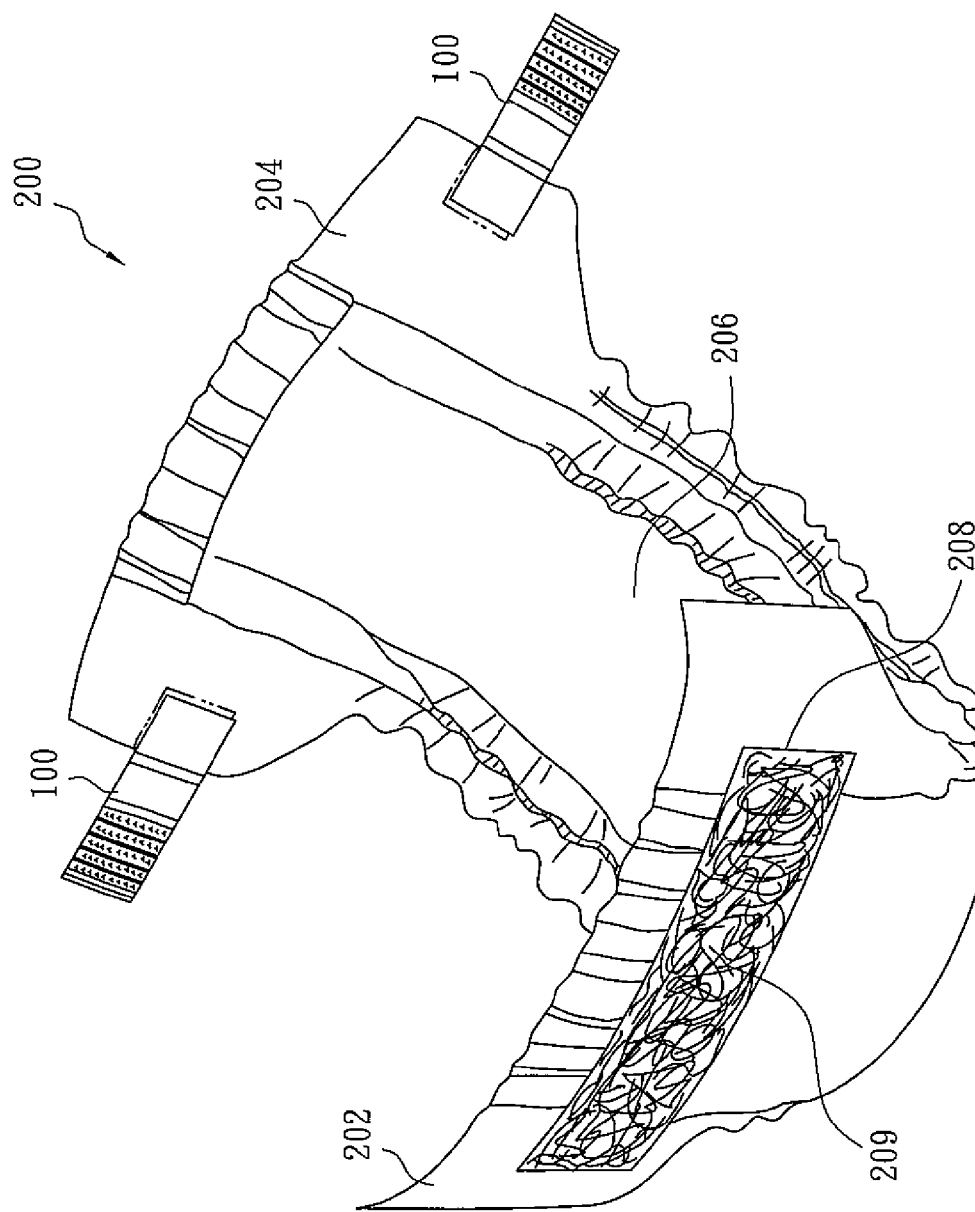
FIG. 8 is a schematic perspective view illustrating a diaper according to a second aspect of the present invention which has fastening straps of FIG. 3 attached thereon.

Referring now to FIG. 8, a diaper (i.e., a disposable absorbing article) 200 according to a second aspect of the present invention which has fastening straps 100 of FIG. 3 attached thereon will be described below. As illustrated in FIG. 8, the diaper 200 mainly includes a front waist portion 202, a rear waist portion 204, a crotch portion 206 extending between the front and the rear waist portions, a loop strap 208 provided on an outer face of the front waist portion 202 and having a plurality of loops 209 formed thereon, and two fastening straps 100 according to the embodiment illustrated in FIG. 3 and described above. Each of the two fastening straps 100 is attached to a lateral side of the rear waist portion 204 for releasably engaging with the loops 209 of the loop strap 208 so as to fastening the disposable absorbing article 200 on to a wear's body. Because the fastening strap 100 of the present invention has a number of binding patterns 124 formed thereon, the overall stiffness of the fastening strap 100 is thus lowered and the softness of fastening strap 100 is thus improved, and this in turn improve the comfortableness of a diaper incorporate the fastening strap 100 of the present invention.

The present invention utilizes a technique that is completely different from the traditional technique for forming fastening strap for a disposable absorbing article. Specifically, in the traditional technique, the fastening strap is formed by using an adhesive layer to bond a hook strap to a backing substrate. The present invention on the other hand forms the fastening strap by securing a hook strap directly to the fabric backing substrate using a fusion bonding process, such as a supersonic welding process or a thermal welding process. Most importantly, because the fastening strap made by the present invention does not include a layer of adhesive across the entire surface of the fastening strap, the fastening strap provided by the present invention has great suppleness.

Although the present invention has been described above according to preferred embodiments of the fastening strap and method illustrated in the accompanying drawings, this does not mean that the scope of the present invention is limited to specific configurations of the fastening strap and the steps or sequences of the method described above. In fact, there exist various modifications and variations under the principle and spirit disclosed above. For instance, although it is illustrated in FIGS. 3-7 that the hooks 122 are dual hook arms type of hooks, other types of hooks, such as mono hook arm hooks, mushroom-headed hooks, are also applicable to the present invention.

It will be apparent to people skilled in this art that many modifications can be made to the disclosed structures without departing from the true scope of the invention defined by the appended claims. Therefore, it is the intent of the appended claims to cover all such variations and modifications as come within the sprit and scope of this invention.

What is claimed is:

1. A fastening strap for a disposable absorbing article comprising:
   a plastic hook strap including a plurality of hooks integrally formed on a face thereof, the plastic hook strap having two lateral side portions, wherein the two lateral side portions are free of hooks;
   two fabric side wings, which are disposed to directly overlay the two lateral side portions respectively; and
   fusion bonds joining the fabric side wings and the two lateral side portions without the use of adhesive.

2. A fastening strap for a disposable absorbing article according to claim 1, wherein the two fabric side wings comprise non-woven fabric, and the fusion bonds comprise supersonic bonds or thermal bonds.

3. A disposable absorbing article comprising:
   a front waist portion;
   a rear waist portion;
   a crotch portion extending between the front and the rear waist portions;
   a loop strap provided on an outer face of the front waist portion, the loop strap having a plurality of loops formed thereon; and
   two fastening straps according to claim 1, each of the fastening straps being attached to a lateral side of the rear waist portion for releasably engaging with the loops of the loop strap so as to fasten the disposable absorbing article onto a wearer's body.

4. A fastening strap for a disposable absorbing article comprising:
   a plastic hook strap including a plurality of hooks integrally formed on a face thereof, the plastic hook strap having two lateral side portions, wherein the two lateral side portions are free of hooks;
   two fabric side wings, which directly overlaid the two lateral side portions respectively; and
   fusion bonds joining the fabric side wings and the two lateral side portions without the use of adhesive; and
   a connecting member having an adhesive film provided at a top face thereof and disposed on one of the fabric side wings such that a distal free edge of said fabric side wing is located at a substantially middle portion of the connecting member, and the connecting member being directly secured to said fabric side wing at the substantially middle portion such that two end sides of the connecting member may be folded toward each other.

5. A fastening strap for a disposable absorbing article according to claim 4, wherein the two fabric side wings comprise non-woven fabric, and fusion bonds comprise supersonic bonds or thermal bonds.

6. A disposable absorbing article comprising:
   a front waist portion;

a rear waist portion;

a crotch portion extending between the front and the rear waist portions;

a loop strap provided on an outer face of the front waist portion, the loop strap having a plurality of loops formed thereon; and two fastening straps according to claim 4, each of the fastening straps being attached to a lateral side of the rear waist portion for releasably engaging with the loops of the loop strap so as to fasten the disposable absorbing article onto a wearer's body.

* * * * *